United States Patent [19]

Denton et al.

[11] Patent Number: 6,034,254

[45] Date of Patent: Mar. 7, 2000

[54] SULFOLANE AND PROCESS THEREFOR

[75] Inventors: C. Stewart Denton; Christopher R. Tully, both of Borger; Max H. Rock, Amarillo; Guy Senatore, Borger, all of Tex.

[73] Assignee: Phillips Petroleum Company, Bartlesville, Okla.

[21] Appl. No.: 09/158,200

[22] Filed: Sep. 22, 1998

[51] Int. Cl.[7] .................................................. C07D 333/48
[52] U.S. Cl. ................................. 549/87; 549/85; 549/84
[58] Field of Search ...................... 549/85, 84, 87

[56] References Cited

U.S. PATENT DOCUMENTS

| | | | |
|---|---|---|---|
| 2,578,565 | 12/1951 | Mahan et al. | 260/332.1 |
| 3,622,598 | 11/1971 | Willis | 260/332.1 |
| 3,770,772 | 11/1973 | Kroll | 549/87 |
| 4,286,099 | 8/1981 | Nash et al. | 549/87 |
| 4,558,138 | 12/1985 | Johnson | 549/87 |
| 4,820,849 | 4/1989 | Diaz et al. | 549/87 |
| 4,861,900 | 8/1989 | Johnson | 549/87 |
| 5,030,737 | 7/1991 | Nash | 549/87 |
| 5,223,101 | 6/1993 | Yeary | 549/87 |
| 5,290,953 | 3/1994 | Clark, Jr. et al. | 549/87 |
| 5,347,018 | 9/1994 | Clark, Jr. et al. | 549/87 |
| 5,512,261 | 4/1996 | Clark, Jr. et al. | 423/242.1 |

OTHER PUBLICATIONS

Oxidation in Organic Chemistry, ACS Monograph 186, (1990).

*Primary Examiner*—Deborah C. Lambkin

[57] ABSTRACT

A process for reducing the odor of sulfolane fluid comprises contacting the fluid with and oxidizing agent under conditions sufficient to effect the substantial reduction of odor in the fluid.

13 Claims, No Drawings

SULFOLANE AND PROCESS THEREFOR

FIELD OF THE INVENTION

This invention relates to a substantially odorless sulfolane and a process for producing the sulfolane compound from a conjugated diene and sulfur dioxide.

BACKGROUND OF THE INVENTION

Odor or odorous material in a fluid often has an adverse effect if the fluid is used in industrial applications. For example, sulfur dioxide or a mercaptan, which may be odorous in a fluid, may induce metal corrosion when the fluid is used in applications requiring the contacting of the fluid with a metal or metal surface. These fluids can be a gas, an aqueous liquid, a non-aqueous liquid, or combinations of two or more thereof such as, for example, a sulfolane compound.

Sulfolane compounds are useful in a variety of industrial applications such as, for example, as solvent in electronic operation, in pesticidal compositions, intermediates in the production of other organic chemicals, selective solvents to separate aromatic compounds from petroleum fractions, and selective solvents in alkylation of olefins.

Sulfolane compounds are generally produced by catalytic hydrogenation of the corresponding sulfolene compounds. The sulfolene compounds are produced by the reaction of a conjugated diene such as, for example, 1,3-butadiene, and sulfur dioxide at elevated temperatures.

However, the sulfolene compounds thus-produced are generally unstable and tend to decompose at mildly elevated temperatures into an unsaturated organic compound and sulfur dioxide. Furthermore, when the sulfolene compounds are used to produce the corresponding sulfolane compounds by catalytic hydrogenation, the initiation of hydrogenation reaction may also increase the temperature enough to result in some decomposition of the sulfolene. Some of these decomposed products often contribute to undesirable odor of the final sulfolane product. If the odorous compound is present in the resulting sulfolane compounds, the sulfolane compounds become undesirable for use in industrial applications. The undesirable odor must be removed or substantially reduced. Therefore, there is an ever-increasing need to develop effective methods of reducing odor in sulfolane compounds thereby greatly improving the appeal of sulfolane compounds for industrial applications.

SUMMARY OF THE INVENTION

An object of the present invention is to provide a process for reducing or substantially reducing the odor in a sulfolane fluid. Also an object of the present invention is to provide a process for preparing a sulfolane fluid having a reduced odor. Another object of the invention is to reduce the odor of sulfolane compounds. A further object of the invention is to produce sulfolane compounds having reduced odor. Still another object of the invention is to provide a substantially odorless sulfolane. Other objects, features and advantages will become more apparent as the invention is more fully disclosed hereinbelow.

According to the present invention, a substantially odorless sulfolane is provided. Also provided is a process for reducing or substantially reducing odor in a sulfolane fluid which comprises contacting the fluid with an oxidizing agent under a sufficient condition to effect the substantial reduction of odor in a sulfolane fluid.

DETAILED DESCRIPTION OF THE INVENTION

According to the present invention, the term "fluid" denotes a gas, a liquid, or combinations thereof. The presently preferred fluid is a crude sulfolane compound which, when produced, generally contains odorous substances dissolved or dispersed in the sulfolane compound.

The preferred process of the present invention for producing a crude sulfolane can comprise the steps of: (1) contacting a conjugated diene with sulfur dioxide under conditions sufficient to synthesize a crude sulfolene compound whereby a mixture of the crude sulfolene compound and impurities comprising unreacted sulfur dioxide is produced; (2) transferring the mixture to an impurities removal reactor containing a solvent; (3) removing the impurities under a reduced pressure to produce an impurities-reduced sulfolene compound; (4) transferring the impurities-reduced sulfolene compound to a hydrogenation reactor; (5) contacting said impurities-reduced sulfolene compound with hydrogen, in the presence of a hydrogenation catalyst, under conditions sufficient to produce a sulfolane compound which can also contain impurities; (6) contacting the sulfolane with an oxidizing agent to produce an odor-reduced or a substantially odorless sulfolane; and (7) optionally recovering said substantially odorless sulfolane.

The term "sulfolene compound" (sometimes referred to as "sulfolenes" or "sulfolene compounds") as employed herein is defined in U.S. Pat. No. 3,622,598, which is incorporated herein by reference. This term includes substituted and unsubstituted 3-sulfolenes and 2-sulfolenes. The preferred sulfolene compound used in this invention is unsubstituted 3-sulfolene, which is commercially available and is produced by the reaction of 1,3-butadiene and sulfur dioxide. The terms "sulfolane" and "sulfolane compounds" are also defined in U.S. Pat. No. 3,622,598. The term "substantial" or "substantially" signifies or refers to more than trivial.

The sulfolene compounds can be prepared by reacting sulfur dioxide with a conjugated diene having the structural formula R—C(R)=C(R)—C(R)=C(R)—R wherein each R can be the same or different and is selected from the group consisting of hydrogen and various organic and/or inorganic radicals which do not interfere with the reaction for producing the sulfolene compound or the subsequent hydrogenation reaction to produce the corresponding sulfolane compound. Inorganic radicals which are suitable include the halogens, hydroxyl groups, and combinations of any two or more thereof. Organic radicals which are preferred include hydrocarbyl substituents having 1 to about 8 carbon atoms per radical.

A presently preferred class of starting materials comprises the conjugated dienes of the structural formula indicated above where each R is individually selected from the group consisting of hydrogen, alkyl, alkenyl, aryl, cycloalkyl, cycloalkenyl, aralkyl, alkaryl, alkylcycloalkyl, and combinations of any two or more thereof. The total carbon content of the conjugated diene is in the range of 4 to about 18.

Representative examples of the conjugated dienes include, but are not limited to, 1,3-butadiene, 2-methyl-1,3-butadiene (isoprene), 2,3-dimethyl-1,3-butadiene, 2,3-diethyl-1,3-butadiene, 3,4-dimethyl-2,4-hexadiene, 2,4-dodecadiene, 2-methyl-1,3-hexadiene, 4-ethyl-1,3-hexadiene, 1-cyclopentyl-1,3-pentadiene, 1-(1-cyclohexene-1-yl)-1,3-butadiene, 2-phenyl-1,3-butadiene, 3-benzyl-1,3-pentadiene, 3-p-tolyl-1,3-pentadiene, and combinations of any two or more thereof. Suitable substituted derivatives of the above illustrated dienes can also be reacted with sulfur dioxide to form desired sulfolene compounds. Examples of such substituted dienes include 2-chloro-1,3-butadiene, 2-methyl-3-chloro-1,3-butadiene, 1-cyano-1,3-butadiene, and combinations of any two or more thereof.

Examples of representative sulfolene compounds include, but are not limited to, 2-methyl-3-sulfolene, 2-sulfolene, 3-sulfolene, 3-methyl-2-sulfolene, 3-methyl-3-sulfolene, 2-methyl-3-sulfolene, 2,4-dimethyl-2-sulfolene, 2,4-dimethyl-3-sulfolene, 3-ethyl-3-sulfolene, and combinations of any two or more thereof.

The term "reactor" used herein is referred to as, unless otherwise indicated, reaction vessel or vessels that can be properly employed in chemical or physical reactions. The choice of a suitable reactor is generally a matter of preference to one ordinarily skilled in the art.

The first step of the process, according to the present invention, is the contacting of a conjugated diene with sulfur dioxide either in the presence or in the absence of a solvent. It can be either a continuous or a batch operation. The molar ratio of sulfur dioxide to the conjugated diene is the ratio that can effect the synthesis of a sulfolene and can be in the range of from about 1:1 to about 2:1, preferably about 1:1 to about 1.5:1, and most preferably 1:1 to 1.2:1. The temperature of the reaction is generally in the range of from about 50° C. to about 150° C., preferably about 60° C. to about 120° C., and most preferably from 65° C. to 80° C. The pressure of the reaction vessel is generally in the range of about 10 psig to about 500 psig, preferably about 20 psig to about 300 psig, and most preferably 30 psig to 120 psig.

The solvent suitable for use in the present invention include, but are not limited to, water, an alcohol, a sulfone, an organic amide, an aromatic compound, and combinations of any two or more thereof. Suitable alcohols include, but are not limited to, methanol, ethanol, propanol, isopropanol, butanol, pentanol, and combinations of any two or more thereof. Suitable sulfone solvents include, but are not limited to, sulfolane, 2-methyl sulfolane, 3-methyl sulfolane, 3-ethyl sulfolane, and combinations of two or more thereof. Suitable organic amide solvents include, but are not limited to, N-methyl-2-pyrrolidone, N,N'-dimethylformamide, and combinations of any two or more thereof. Examples of suitable aromatic compounds include, but are not limited to, toluene, xylenes, and combinations thereof. The weight ratio of the solvent, if present, to the conjugated diene is generally in the range of about 0.05:1 to about 1,000:1, preferably 0.5:1 to 10:1.

The order of addition of reactants to the reaction vessel is not important. Generally, the conjugated diene is added to the reaction vessel which already contains the sulfur dioxide to form a reaction mixture. The reaction mixture is allowed to react for a sufficient time, generally about 2 hours to about 24 hours, to allow substantial completion of the reaction to produce a reaction mixture comprising the sulfolene compound.

Upon the desired completion of the reaction, a molten reaction effluent is transferred to an impurities removal vessel (sometimes referred to as a sulfur dioxide removal vessel) which contains a solvent. The scope of the solvent is the same as described above in the first step of the process. The amount of solvent required is a sufficient amount to provide a fluid solution and the weight ratio of the solvent to the sulfolene is generally in the range of about 1:1 to about 1:20. Water is the presently preferred solvent because it promptly decreases the freezing point of the molten sulfolene compound produced in the first step so that decomposition of the sulfolene compound is minimized. The temperature of the molten reaction mixture and the solvent in the removal reactor is maintained at about 35° C. to about 85° C., preferably about 35° C. to about 70° C., and most preferably 40° C. to 65° C. to minimize the decomposition of sulfolene and the formation of undesirable polymers.

After completion of the transfer, impurities including unreacted sulfur dioxide and the sulfur dioxide produced as a result of decomposition of the sulfolene compounds where the sulfur dioxide may be dissolved in the solvent employed are removed by sparging an inert gas to the contents in the removal vessel, under a vacuum in the range of about 1 mmHg to about 500 mmHg, preferably about 10 mmHg to about 300 mmHg, and most preferably 20 mmHg to 100 mmHg. The inert gas is generally sparged at a rate in the range of about 1 to about 100 standard cubic feet per hours (scfh), preferably about 1 to about 50 scfh, and most preferably 1 to 10 scfh. The time required for substantially removing the sulfur dioxide varies, depending on the concentration of the sulfur dioxide, the temperature, nitrogen sparged, and the pressure applied, and is generally about 10 minutes to about 10 hours. The temperature for removal of the sulfur dioxide is generally in the range of temperature disclosed hereinabove for the removal reactor. Though it is not necessary to stir the reaction mixture during the sulfur dioxide removal, a mechanical mixing, such as stirring, of the reaction mixture can be used to facilitate the removal of sulfur dioxide. A further enhancement of the sulfur dioxide removal can be accomplished by the process of the present invention as disclosed above.

Upon removing substantially all sulfur dioxide, a sulfolene compound having substantially reduced sulfur dioxide and other volatile impurities is produced. The sulfolene compound is thereafter transferred to a hydrogenation reactor followed by addition of a suitable hydrogenation catalyst. Suitable catalysts include any of those known in the art to be useful in the catalytic hydrogenation of sulfolenes to sulfolanes. A preferred class of hydrogenation catalysts are those which comprise the metal hydrogenation catalysts, such as those containing or consisting of nickel, cobalt, copper, platinum, palladium or mixtures of these metals with themselves or with other metals such as iron, zinc, chromium, cadmium, and mixtures thereof. These metals may be used in finely divided form such as, for example, Raney nickel, or may be suitably supported on a support such as kieselguhr, aluminum oxide, and diatomaceous earth. These catalysts can be prepared in any suitable manner known to one skilled in the art. The amount of catalyst utilized will vary with the catalyst but will generally be in the range of about 0.1 to about 20 weight percent based on the weight of sulfolene compounds to be hydrogenated.

According to the present invention, the total hydrogenation catalyst required is added in about 1–10 increments to the hydrogenation reactor containing the sulfolene compounds. The total hydrogenation catalyst required is the amount of catalyst necessary to substantially hydrogenate all sulfolene compounds in the hydrogenation reactor. This can be done by monitoring the hydrogen uptake. Hydrogen can be constantly introduced into the hydrogenation reactor and monitored by heat release or by pressurizing the reactor up and watching the pressure decrease. Additional catalyst is added when the hydrogen uptake stops or slows down significantly.

The hydrogenation of the sulfolene compounds is carried out by the conditions well known to one skilled in the art. An example is disclosed in U.S. Pat. No. 3,622,598, which is incorporated herein by reference.

Following completion of the hydrogenation reaction, a sulfolane compound can be recovered by any conventional procedures. Generally, the reaction gases are vented from mixtures and then the reaction mixture is filtered to remove the spent hydrogenation catalyst followed by fractionation of the filtered reaction mixture to remove solvent and unreacted sulfolene compound. The fractionation (purification) is performed in three steps. First, the sulfolane can be dehydrated at about 100° C. and atmospheric pressure. Secondly, the sulfolane can be cooked at a temperature in the range of from bout 100° C. to about 300° C., preferably about 140° C. to about 250° C., and most preferably 170° C. to 200° C. under a reduced pressure of about 50 to about 200 mmHg for about 1 to about 15 hours, preferably about 1 to about 12 hours, and most preferably 1 to 10 hours, to effect the decomposition of residual sulfolene and removal of butadiene and sulfur dioxide. Afterwards, the sulfolane can be further purified by distillation at a reduced pressure in the range of from about 1 mmHg to about 200 mmHg, and preferably 10 mmHg to 50 mmHg and 130° C. to about 250° C., and most preferably 160° C. to 180° C. for a period as disclosed immediately hereinabove.

According to the invention, an odorous sulfolane fluid or sulfolane-containing fluid is contacted with an oxidizing agent under a condition effective to substantially reduce the odor of the fluid. Any oxidizing agent which can effect the reduction of the odor of the fluid can be used. Examples of suitable oxidizing agents include, but are not limited, to, hydrogen peroxide, peroxy acids, manganese dioxide, ferric chloride, air, dichromates, chlorochromates, periodates, perchlorates, oxygen, and combinations of two or more thereof. The presently preferred oxidizing agent is hydrogen peroxide for it is readily available and easy to use.

The condition can include a temperature that can effect a reduction of the odor in the fluid. Generally, the temperature can be in a range of from about 25° C. to about 400° C., preferably about 35° C. to about 350° C., and most preferably 45° C. to about 250° C. The time required for carrying out the process of the invention is a sufficient time required to effect the reduction of odor in a sulfolane fluid and generally depends on the desired reduction. Generally, it depends on the temperature and can be in a range of from about 1 minute to about 100 hours, preferably about 5 minutes to about 80 hours, most preferably 10 minutes to 75 hours. The process of the invention can be carried out under any pressure, i.e., reduced or elevated pressure, so long as the pressure can effect a reduction in odor in a sulfolane fluid. Water, about 1–10 weight % based on the substantially odorless sulfolane, can be added to the sulfolane.

The following examples are presented to further illustrate the invention and are not to be construed to unduly limit the scope of the invention.

EXAMPLE I

This is an example showing a process for preparing sulfolane compounds.

The runs were carried out as follows. A 2 gallon stainless steel reactor which contained a heel of 4750 grams of sulfolene at 74° C. was charged with 4.2 g of dimethylamine. Sulfur dioxide (1412 g or 22.06 moles) and 1,3-butadiene (1135 g or 20.02 moles) were pumped in at a rate of about 4 to 6 grams per minute while maintaining operating temperature with an external electric heater. The pressure during the above feedstock addition increased to about 160 psig (1102 kPa) by the end of the butadiene addition (e.g., 3.0 hours). The reaction mixture was kept at 74° C. with stirring for 7 to 24 hours while the pressure slowly decreased to about 80 psig (551 kPa).

A portion of the reaction mixture was then transferred, using a dip tube, to an impurities removal vessel containing 1000 g of water at 50° C., leaving a heel of 4750 g of sulfolene.

A 100 mm Hg vacuum was applied to the impurities removal reactor for 2 to 6 hours, with continuous mixing to remove most of the sulfur dioxide, while the reactor temperature was maintained at 50° C. The $SO_2$-reduced sulfolene/water mixture was transferred to a hydrogenation reactor prior to adding catalyst. Raney nickel catalyst (150 g) was weighed out on a scale, kept wet to prevent it from rapidly oxidizing and charged to the hydrogenation reactor. The reactor was pressured to 400 psig with hydrogen. Hydrogen uptake was monitored by pressure decrease. When the pressure had decreased to 200 psig, the reactor was charged back with hydrogen to 400 psig. When the pressure ceased to fall, the hydrogenation of sulfolene was considered complete. Since the hydrogenation heat of reaction is 32.1 Kcal per gram mole, the reactor medium was maintained at 50° C. by internal cooling coils with cool water. Total sulfolane produced was about 2000 g and had a characteristic odor.

EXAMPLE II

This example illustrates the process of the invention.

Hydrogen peroxide was added to sulfolane produced by the process described in Example I. The quantity of hydrogen peroxide added was an amount that resulted in 0.25 weight % of hydrogen peroxide in the sulfolane. The hydrogen peroxide-sulfolane mixture was subject to a treatment at 140° F. for 24 hours to produce sulfolane that is substantially odorless.

The results shown in the above examples clearly demonstrate that the present invention is well adapted to carry out the objects and attain the ends and advantages mentioned as well as those inherent therein. While modifications may be made by those skilled in the art, such modifications are encompassed within the spirit of the present invention as defined by the disclosure and the claims.

That which is claimed is:

1. A process comprising (1) contacting a conjugated diene with sulfur dioxide under conditions sufficient to synthesize a crude sulfolene compound whereby a mixture of said crude sulfolene compound and impurities comprising unreacted sulfur dioxide is produced; (2) transferring said mixture to an impurities removal reactor containing a solvent; (3) removing said impurities under a reduced pressure to produce an impurities-reduced sulfolene compound; (4) transferring said impurities-reduced sulfolene compound to a hydrogenation reactor; (5) contacting said impurities-reduced sulfolene compound with hydrogen, in the presence of a hydrogenation catalyst, under conditions sufficient to produce a sulfolane compound; and (6) contacting said sulfolane with an oxidizing agent to produce an odor-reduced or substantially odorless sulfolane compound.

2. A process according to claim 1 further comprising recovering said odor-reduced or substantially odorless sulfolane compound.

3. A process according to claim 1 wherein said oxidizing agent is selected from the group consisting of hydrogen peroxide, peroxy acids, manganese dioxide, ferric chloride, air, dichromates, chlorochromates, periodates, perchlorates, oxygen, and combinations of two or more thereof.

4. A process according to claim 1 wherein said oxidizing agent is hydrogen peroxide.

5. A process according to claim 2 wherein said oxidizing agent is hydrogen peroxide.

6. A process according to claim 1 wherein said contacting in step (6) is carried out at a temperature in the range of from about 25° C. to about 400° C.

7. A process according to claim 4 wherein said contacting in step (6) is carried out at a temperature in the range of from 45° C. to 250° C.

8. A process comprising (1) contacting a conjugated diene with sulfur dioxide under conditions sufficient to synthesize a crude sulfolene compound whereby a mixture of said crude sulfolene compound and impurities comprising unreacted sulfur dioxide is produced; (2) transferring said mixture to an impurities removal reactor containing a solvent; (3) removing said impurities under a reduced pressure to produce an impurities-reduced sulfolene compound; (4) transferring said impurities-reduced sulfolene compound to a hydrogenation reactor; (5) contacting said impurities-reduced sulfolene compound with hydrogen, in the presence of a hydrogenation catalyst, under conditions sufficient to produce a sulfolane compound; and (6) contacting said sulfolane compound with an oxidizing agent at a temperature in the range of from about 25° C. to about 400° C. to produce an odor-reduced or substantially odorless sulfolane compound wherein said oxidizing agent is selected from the group consisting of hydrogen peroxide, peroxy acids, manganese dioxide, ferric chloride, air, dichromates, chlorochromates, periodates, perchlorates, oxygen, and combinations of two or more thereof.

9. A process according to claim 8 further comprising recovering said odor-reduced or substantially odorless sulfolane compound.

10. A process according to claim 8 wherein said oxidizing agent is hydrogen peroxide.

11. A process according to claim 9 wherein said oxidizing agent is hydrogen peroxide.

12. A process comprising (1) contacting a conjugated diene with sulfur dioxide under conditions sufficient to synthesize a crude sulfolene compound whereby a mixture of said crude sulfolene compound and impurities comprising unreacted sulfur dioxide is produced; (2) transferring said mixture to an impurities removal reactor containing a solvent; (3) removing said impurities under a reduced pressure to produce an impurities-reduced sulfolene compound; (4) transferring said impurities-reduced sulfolene compound to a hydrogenation reactor; (5) contacting said impurities-reduced sulfolene compound with hydrogen, in the presence of a hydrogenation catalyst, under conditions sufficient to produce a sulfolane compound; and (6) contacting said sulfolane with hydrogen peroxide at a temperature in the range of from 45° C. to 250° C. to produce an odor-reduced or substantially odorless sulfolane compound.

13. A process according to claim 1 further comprising recovering said odor-reduced or substantially odorless sulfolane compound.

* * * * *